United States Patent [19]

Takanishi

[11] Plant 4,827

[45] Feb. 23, 1982

[54] PEACH TREE

[76] Inventor: Yutaka T. Takanishi, 10148 S. Petersen, Reedley, Calif. 93654

[21] Appl. No.: 159,301

[22] Filed: Jun. 13, 1980

[51] Int. Cl.[3] ..... A01H 5/03

[52] U.S. Cl. ..... Plt./43

[58] Field of Search ..... Plt./43

[56] References Cited

U.S. PATENT DOCUMENTS

P.P. 4,064 6/1977 Minami ..... Plt./43

*Primary Examiner*—Robert E. Bagwill

*Attorney, Agent, or Firm*—Roger B. Webster

[57] ABSTRACT

A peach tree which is large, vigorous, spreading, open, vase-formed, hardy, foliated with large, lanceolate, acutely pointed leaves having a coarsely serrate margin and alternate, reniform glands, bears medium size, obtuse, plump flower buds, blooms early with large, pink flowers, and is a regular and productive bearer of early-ripening, medium size, clingstone fruit of globose form with unequal sides, the fruit—somewhat variable in both size and form—having yellow flesh, yellow skin substantially overspread with red in maturity, and a large stone.

1 Drawing Figure

BACKGROUND OF THE VARIETY

1. Field of the Discovery

The present new and distinct variety of peach tree is embraced by Class 43, Plants, of the U.S. Patent Office Manual of Classification.

2. Prior Varieties

Among the existent varieties of peach trees which are known to me, I make particular reference to the Springcrest (an unpatented U.S.D.A. variety)—mentioned hereinafter in this specification.

ORIGIN OF THE VARIETY

The present variety of peach tree was discovered by me growing as a bud sport limb on a Springcrest tree in an orchard on my ranch located near Reedley, Fresno County, Calif., and the fruit of which bud sport limb ripened substantially earlier than the remaining fruit on such Springcrest tree. Such bud sport limb was maintained, by me, under careful and continuing observation, and, in continuing recognition of the early ripening characteristic of its fruit, I determined—because of its potential commercial value—to effect asexual reproduction of the variety represented by such bud sport limb.

ASEXUAL REPRODUCTION OF THE VARIETY

The present variety of peach tree was asexually reproduced by me on my ranch located as aforesaid; the reproductions, accomplished by budding, having run true to the original bud sport limb in all respects.

SUMMARY OF THE VARIETY

The herein-claimed variety of peach tree is large, vigorous, spreading, open, vase-formed, hardy, foliated with large, lanceolate, acutely pointed leaves having a coarsely serrate margin and alternate, reniform glands, bears medium size, obtuse, plump flower buds, blooms early with large, pink flowers, and is a regular and productive bearer of early-ripening, medium size, clingstone fruit of globose form with unequal sides, the fruit—somewhat variable in both size and form—having yellow flesh, yellow skin substantially overspread with red in maturity, and a large stone.

The herein-claimed variety of peach tree, while having general similarity to the Springcrest in tree and fruit, is distinctively characterized—in comparison—by ripening, for harvest, seven to ten days earlier.

BRIEF DESCRIPTION OF THE DRAWING

The drawing is an illustration, by photographic reproduction in color, of a number of separate fruit of the variety; one such fruit being half cut away to expose the stone and the latter remaining in place.

DESCRIPTION OF THE VARIETY

The botanical details of this new and distinct variety of peach tree—with color definitions (except those in common color terms) referenced to Maerz and Paul Dictionary of Color (second edition)—are as follows:

Tree:
- *Size.*—Large.
- *Vigor.*—Vigorous.
- *Growth.*—Spreading.
- *Density.*—Open.
- *Form.*—Vase-formed.
- *Hardiness.*—Hardy.
- *Production.*—Productive.
- *Bearing.*—Regular bearer.

Trunk:
- *Size.*—Stocky.
- *Texture.*—Medium.

Branches:
- *Size.*—Medium.
- *Texture.*—Smooth.
- *Color.*—Chukker Brown (15-C-8).
- *Lenticels.*—Number: numerous. Average size: 1–2 mm.×3–5 mm.

Leaves:
- *Size.*—Large. Average length — 170 mm. Average width — 42 mm.
- *Form.*—Lanceolate. Acutely pointed.
- *Thickness.*—Medium.
- *Texture.*—Smooth.
- *Color.*—Top side — dark green (24-L-7). Under side — lighter green (22-K-7).
- *Margin.*—Coarsely serrate.

*Petiole.*—Medium length (average — 12 mm.). Medium thickness (average — 3 mm.).

*Glands.*—Average number — 2-3. Alternate. Medium size — (average — 1 mm.). Reniform. Quaker green (23-L-4).

Flower buds:

*Size.*—Medium.

*Form.*—Obtuse. Plump.

*Pubescence.*—Pubescent.

*Color.*—Lowerside edges: pink (50-F-3). Lowerside bases: pink (50-I-6).

Flowers:

*Blooming period.*—Date of first bloom: Feb. 27th. Date of full bloom: Mar. 5th. Petal fall: Mar. 10th. Early, as compared with other varieties.

*Size.*—Large. Average — 34 mm. in diameter. Pistil — 1. Stamen — 47-48.

*Color.*—Upperside edge: pink (50-F-4). Upperside base: pink (50-H-6).

Fruit:

*Maturity when described.*—Ripe — May 25th.

*Date of first picking.*—7 to 10 days earlier than Springcrest.

*Date of last picking.*—With first picking of Springcrest.

*Size.*—Medium. Variable. Average diameter axially — 65-68 mm. Average transversely in suture plane — 70-72 mm.

*Form.*—Variable. Globose with unequal sides.

*Suture.*—Distinct. Shallow. Extends from base over entire circumference.

*Ventral surface.*—Rounded slightly.

*Cavity.*—Abrupt. Average depth — 10 mm. Average breadth — 15 mm.

*Base.*—Rounded.

*Apex.*—Rounded. Depressed.

*Pistil point.*—Murconate.

*Stem.*—Average length — 10 mm. Average caliper — 5 mm.

Skin:

*Thickness.*—Medium.

*Texture.*—Medium.

*Tenacity.*—Tenacious to flesh.

*Tendency to crack.*—None.

*Down.*—Scant.

*Color.*—Ground color — golden yellow (9-J-7). Blush color — Kazak red (7-L-9).

Flesh:

*Color.*—golden yellow (9-K-7). Surface of pit cavity: golden yellow (9-K-7).

*Juice.*—Abundant.

*Texture.*—Medium. Fine. Melting.

*Fibers.*—Few. Fine.

*Ripens.*—Evenly.

*Flavor.*—Subacid. Delicate.

*Aroma.*—Distinct.

*Eating quality.*—Good.

Stone:

*Type.*—Cling. Adheres to flesh over entire surface.

*Fibers.*—Long.

*Size.*—Large. Average length — 40 mm. Average breadth — 25 mm. Average thickness — 18 mm.

*Form.*—Oval.

*Base.*—Oblique.

*Hilum.*—Narrow.

*Apex.*—Acute.

*Sides.*—Unequal. Flattened.

*Surface.*—Irregularly furrowed throughout.

*Ridges.*—Rounded toward apex.

*Ventral edge.*—Thin, with wing in middle.

*Dorsal edge.*—Full, with broad groove throughout.

*Color.*—Inca Gold (11-J-7).

*Tendency to split.*—Slight.

Use: Market; dessert.

Keeping quality: Good.

Shipping quality: Good.

The peach tree and its fruit herein described may vary in slight detail due to climatic and soil conditions under which the variety may be grown; the present description being of the variety as grown in the Central Valley of California.

I claim:

1. A new and distinct variety of peach tree, substantially as illustrated and described, which is generally similar in tree and fruit to the Springcrest variety, but distinctively characterized, in comparison, by fruit which ripens, for harvest, seven to ten days earlier.

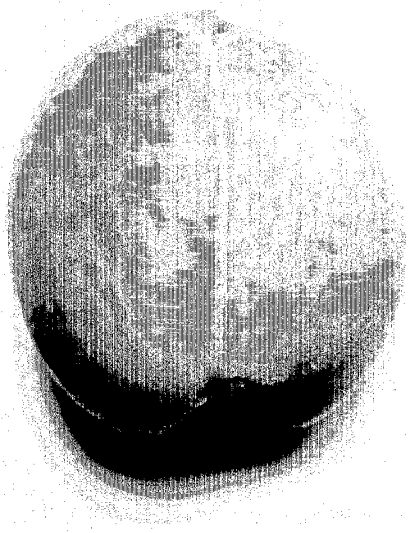
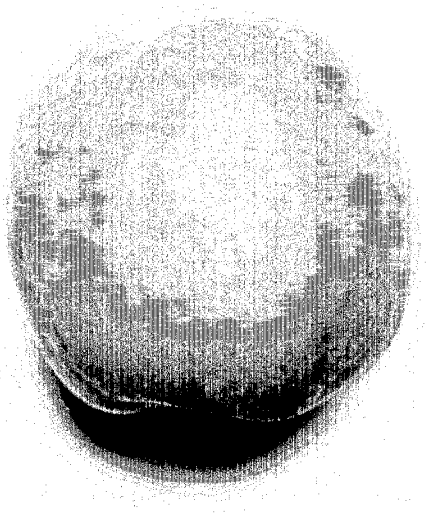
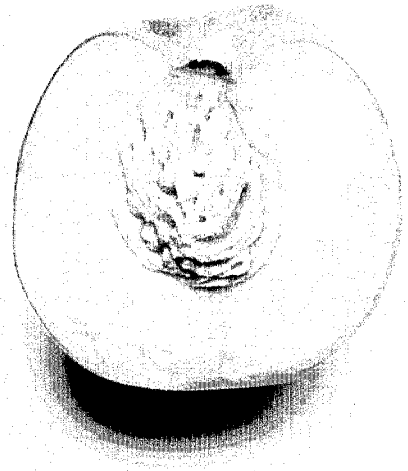

* * * * *